United States Patent [19]

Zook

[11] Patent Number: 5,098,421

[45] Date of Patent: * Mar. 24, 1992

[54] VISCOELASTIC GEL FOOT PADDING AND MEDICATING DEVICE

[76] Inventor: Gerald P. Zook, 1860 Friendly, Eugene, Oreg. 97402

[*] Notice: The portion of the term of this patent subsequent to Jun. 27, 2006 has been disclaimed.

[21] Appl. No.: 421,644

[22] Filed: Oct. 16, 1989

[51] Int. Cl.⁵ .............................................. A61F 13/15
[52] U.S. Cl. ..................... 604/367; 604/307
[58] Field of Search ......... 604/367, 304–307, 604/20; 128/155, 156, 112.1, 113.1, 114.1, 893, 894, 165; D24/49; 428/343

[56] References Cited

U.S. PATENT DOCUMENTS

| | | | |
|---|---|---|---|
| 1,630,596 | 5/1927 | Banff | 604/307 |
| 2,432,541 | 12/1947 | Peck | 604/307 |
| 3,783,869 | 1/1974 | Schnipper | 604/304 |
| 4,787,888 | 11/1988 | Fox | 604/20 |
| 4,842,931 | 6/1989 | Zook | 428/343 |

Primary Examiner—Randy C. Shay
Assistant Examiner—G. Gualtieri
Attorney, Agent, or Firm—John F. Ingman

[57] ABSTRACT

A padding and medicating device for the human foot comprising a sheet structure, preferably of an elastic fabric material and partially coated on one surface with a pressure sensitive adhesive, in combination with a pad of viscoelastic gelatinous material impregnated onto a portion of the same surface of the sheet structure as the pressure sensitive adhesive. The pad of viscoelastic gelatinous material is preferably made with an oleaginous plasticizer such as Mineral Oil USP, and may contain one or more pharmacologically active agents. The sheet structure is oil impervious or a separating layer of material impervious to the oleaginous plasticizer is incorporated on either surface of the sheet structure adjacent to the area of the sheet structure to be impregnated with the viscoelastic gelatinous material to prevent the oleaginous plasticizer from bleeding onto the sock or shoe of the wearer. Ideally the viscoelastic gelatinous material is thermoplastic, ultrasoft, able to stretch to many times its relaxed dimensions without tearing, and capable of bleeding a significant amount of a liquid hydrocarbon plasticizer such as Mineral Oil USP onto the skin of the wearer. The present invention can also function as a blister dressing which is able to internally absorb horizontal shearing forces when the gel is employed in thin layers. An alternative embodiment comprising only the viscoelastic gel molded into the shape of a toe spacer, crest pad, corn or bunion pad and the like is also contemplated.

12 Claims, 1 Drawing Sheet

VISCOELASTIC GEL FOOT PADDING AND MEDICATING DEVICE

FIELD OF INVENTION

This invention relates to a foot padding and medicating devices and specifically a foot padding and medicating device of the type described in U.S. Pat. No. 4,842,931 incorporating oleaginous viscoelastic gels, methods of manufacture, and means of affixing the devices to the foot of the wearer.

BACKGROUND OF THE INVENTION—DESCRIPTION OF PRIOR ART

The human foot is a highly and complex dynamic structure. It is a biomechanically efficient structure capable of numerous intricate articulations which enable it not only to bear weight but to absorb, channel, and return the energy that makes locomotion possible. These articulations, collectively referred to as pronation and supination, produce a tremendous amount of motion within the foot. In addition, when there is a biomechanical or structural abnormality within the foot, excessive motion and/or orthopedic structural deformities such as bunions, hammertoes, and exostoses can result. Shoes are a relatively recent invention designed to protect and support the foot. Unfortunately, most shoes are not designed to accommodate either the physical structure or dynamic motion of the human foot as it progresses repeatedly through the gait cycle. Many shoes are made of rigid leather or unyielding synthetic materials that create pressure and friction against the foot. When this happens numerous pathological lesions can result. For example, when a person has an orthopedic deformity such as a bunion, hammertoe, or exostosis, discrete pressure points can develop between the underlying osseous structure and the unyielding shoe gear. This results in pain and inflammation of the soft tissue interposed between these two rigid structures. In extreme cases, ulcerations can occur. In milder conditions, this pressure and irritation can result in bursa formation or more frequently in thick, hard, and dessicated stratum cornium commonly known as corns or calluses. As these hard, dry keratotic lesions build up, they create even more pressure, irritation, and pain for the afflicted shoe wearer. In other cases, it is friction between the soft tissue and relatively rigid shoe gear that results in irritation, blister formation, and in extreme cases, skin ulceration and infection.

The art of padding and medicating foot lesions is old and crowded. Over the past 100 or so years there have been numerous unsuccessful attempts to address the need to protect the human foot from the ravages of shoe gear. Likewise, there have been numerous attempts to provide a drug delivery system for the human foot that would allow therapeutic agents to be delivered to the foot without the medication being immediately absorbed or rubbed off the skin by socks or shoes. As described in U.S. Pat. No. 4,842,931, the present invention embodies a device which is simultaneously able to pad an orthopedic deformity, dissipate pressure and friction in a superior manner, and provide a dose of a softening and lubricating agent such as mineral oil, or even a pharmacologically active drug, to the cutis of the afflicted shoe wearer by utilizing an oleaginous viscoelastic gel. The present invention teaches a means for preventing the oil fraction of the gel from bleeding out of the bandage which may result in staining of the sock, shoe, or other article of clothing.

Historically most foot protecting devices have been made of compressible materials such as felt, foam rubber, and the like. For example, Duckworth in U.S. Pat. No. 707,089 teaches a corn shield with an interior cavity designed to relieve pressure and irritation. Lepper in U.S. Pat. No. 832,550 teaches an insole with built-in corn pads and mentions the use of medicated pads. Schultz in U.S. Pat. No. 893,876 describes a foot protector made of multiple layers of material, such as felt, which can be customized by removing one or more of the layers. U.S. Pat. Nos. 2,646,795 & 2,827,049 and Canadian Patents 570,208, 556,497, & 581,808 to Scholl, teach various foot protective pads made of foamed latex or felt and contoured to accommodate a pedal deformity. All of these inventions are made of compressible materials and thus are subject to several intrinsic limitations. When compressible materials, such as felt or foam rubber, are subjected to pressure, air is forced out of the interstices of the material and the volume of the padding material decreases. Concomitantly, the density of the padding material increases. For example, a foam rubber corn pad worn on a digit inside a tightly fitting shoe can be compressed to the point where its density approaches that of a piece of solid rubber. In this condition, the pad of compressible material, functions poorly as a dissipator of pressure and especially horizontal shearing (frictional) forces. By contouring the padding material, which requires multiple manufacturing procedures, devices with limited pressure dissipating but practically no friction dissipating properties can be produced. This problem of friction was addressed by Thompson in U.S. Pat. No. 2,943,623. Thompson teaches a skin plaster made of thin strips of tetrafluroethylene which has an extremely low coefficient of friction. Unfortunately, Thompson's skin plaster lacked the ability to pad or medicate foot lesions. Several inventions have been described which will provide medication to the foot but they all suffer from one or more objections. George's in U.S. Pat. No. 281,487 describes a corn or bunion shield made of layers of leather or chamois with a central aperture and mentions the incorporation of oiled silk to soften and lubricate a corn or callus. Rightmire in Reissue U.S. Pat. No. 13,608 teaches a device consisting of small medication containing cups that are secured to the digit by an elastic strap-like member. These cups can be filled with medication. Prisk in U.S. Pat. No. 2,561,071 describes a holder for subcutaneous administration of medicaments. All of these inventions require that medication be deposited in a receptical and the receptical (the dressing) then be affixed to the wearer. In contrast, the present invention teaches a device where the medication (i.e., Mineral Oil USP) or a pharmacologically active agent is actually a constituent of the viscoelastic gel pad.

Viscoelastic gels have been used in medicine as decubitus ulcer dressings, physical therapy devices such as hand exercisers, and prosthetics such as artificial breast implants King in U.S. Pat. No. 3,419,006 teaches a hydrogel made from polyethelyene oxide which is 96% water. This material is marketed as a blister dressing under the name Second Skin ® (Spenco Medical Corporation, Waco, Tex.). Unfortunately, Second Skin ® is impractical to use as a blister dressing because it is very difficult to attach to the skin it will migrate in response to shoe pressure, and it will dry out when exposed to the air. Spence in U.S. Pat. No. 3,548,420 teaches cushion structures made from an organosiloxane gel. Spence's gel lacks an intrinsic medicinal liquid fraction such as Mineral Oil USP, and furthermore, lacks the elasticity to internally absorb horizontal shearing (frictional forces) when applied in very thin layers, an important consideration for a device worn inside a shoe. Spence in U.S. Pat. No. 4,756,949 teaches a method for producing pad structures made from a PVC resin and a dialkylphthalate plasticizer. Again, these pads impart no medicinal substances to the wearer. Shaw in U.S. Pat. No. 4,380,569 teaches a light weight gel structure which incorporates glass microspheres. Sieverding teaches a hydrophlyic elastomeric pressure sensitive adhesive in U.S. Pat. No. 4,699,146.

OBJECTS AND ADVANTAGES

Accordingly, a primary object of the present invention is to provide a foot protective device which incorporates a viscoelastic gel pad capable of bleeding a therapeutic agent such as Mineral Oil USP onto a hard dry keratotic lesion and thereby softening and lubricating the keratotic lesion which at the same time preventing the oil fraction of the gel from bleeding out of the bandage. A further object of this invention is to provide a foot protective and medicating device which is able to deliver a therapeutically significant dose of a pharmacologically active substance to a foot lesion by incorporating a pharmacologically active agent into the liquid plasticizer fraction of the viscoelastic gel such that it will bleed out of the gel and onto the foot lesion along with the liquid fraction.

A further object of the present invention is to provide a foot padding device which is able to equalize pressure around an orthopedic deformity such as a bunion, hammertoe, or exostosis in a superior hydraulic manner. By this, I mean that when external pressure from shoegear presses the ultrasoft viscoelastic gel against the irregularly shaped surface of the orthopedic deformity the gel will flow away from the areas of increased pressure and will thus dissipate the pressure throughout the mass of the gel pad in a superior manner.

Yet another object of the present invention is to provide a friction or blister dressing by utilizing an extremely elastic gel which is able to internally dissipate frictional forces between the skin and footwear even when employed in very thin layers.

Still yet another object of the present invention is to provide a foot padding and medicating device with means for attachment to the foot of the wearer.

A still further object of the present invention is to teach methods of manufacture for the above mentioned foot padding and medicating devices. Still further objects and advantages will become apparent from a consideration of the ensuing description and drawings

DESCRIPTION OF THE INVENTION

Figure 1:
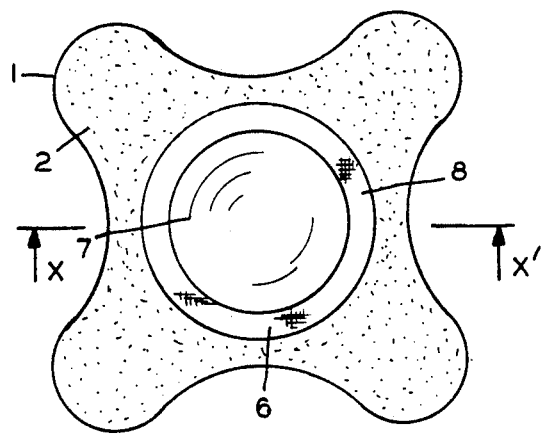
FIG. 1 is a view looking down on the adhesive surface of the bandage.
Figure 2:
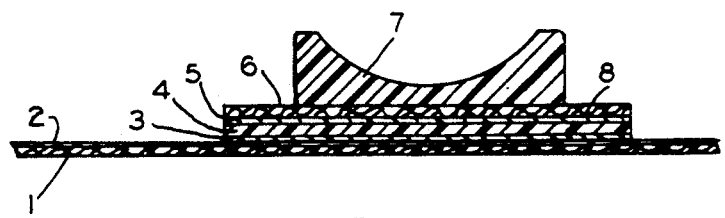
FIG. 2 is a sectional view of the bandage taken at line x—x$^1$ in FIG. 1.

FIG. 1 illustrates the surface of the invention intended for contact with the skin of the wearer. In the shown embodiment the fabric bandage 1 has four adhesive winged projections to secure the bandage to the skin. The fabric of the bandage is preferably an elastic fabric such as spandex or the fabric used in Elastoplast ® (Biersdorf Medical Program, Norwalk, Conn.) bandages. The gel pad 7 is impregnated onto the fabric bonding surface 6 of the backing material 8. The circumference of the backing material 8 is greater than the circumference of the gel pad 7 to allow for the increased diameter of the gel when pressure or shearing forces are applied to the bandage. FIG. 2 is a cross-sectional view of the same embodiment of the present invention as shown in FIG. 1 and taken at line x—x$^1$. The gel pad 7 is shown to be on the same surface of the fabric bandage 1 as the adhesive 2. The gel pad 7 is directly impregnated onto a fabric bonding surface 6 of the backing material. This fabric bonding member can be any fibrous or porous sheet material such as flannel, felt, cotton, polyester or the like, which will allow for good bonding during the impregnation process described later in this specification and also is somewhat elastic in nature. The fabric bonding surface 6 of the backing material is affixed to a sheet member 4 by means of a layer of adhesive 5. Sheet member 4 is preferably a layer of oil impervious material such as acetate, plastic, silicone rubber or the like. In one embodiment of the invention, the sheet member 4 is elastic so that the entire invention is capable of stretching. Ideally sheet member 4 is from about 1 mil to 10 mils thick. The adhesive 5 which bonds fabric 6 to oil impervious sheet 4 is preferably a medical grade silicone adhesive which will not be soluabilized by the oil fraction of the gel pad 7. Sheet member 4 is secured to the fabric bandage 1 by means of a second layer of adhesive 3. As illustrated in FIG. 2, the gel pad 7 can be contoured during manufacture resulting in a pad of variable thickness. Similarly, the gel pad can be contoured to form a pad of variable thickness with a central area of zero thickness where an aperture can be created. The gel pad 7 can also be of uniform thickness. Thickness of the pad can be from zero to 1 cm. or thicker if desired. In the preferred embodiment of the present invention the gel pad is made of a thermoplastic, viscoelastic composition with an oleaginous plasticizer or liquid fraction. Examples of such materials are the thermoplastic elastomer gelatinous compositions taught by Chen in U.S. Pat. No. 4,369,284. Ideally this oleaginous liquid fraction is a petroleum derived hydrocarbon with about 15 to about 24 carbon atoms. Mineral Oil, USP and Light Mineral Oil, N.F. are two such petroleum derived hydrocarbons.

In the preferred embodiment the circumference of the backing material is greater than the circumference of the gel pad 7 such that a border or rim 8 of backing material projects radially outward from the periphery of the gel. This border of backing material allows for the gel to flow radially outward when subjected to pressure or friction and still not come in contact with the adhesive surface of the bandage 2.

My current method of manufacturing this affixable padding material is as follows: Beginning with a bandage such as a Coverlet ® No. 385 (Biersdorf Medical Program, Norwalk, Conn.), the fabric pad of the bandage is stripped off. These cleaned bandages are then set aside. Next, a sheet of clear acetate material of from 1.0 to 10.00 mils is obtained and sanded on both surfaces with coarse sandpaper. One surface of this acetate sheet is coated with a silicone adhesive. Before this silicone adhesive can dry, a sheet of thin flannel cloth of approximately the same size as the acetate sheet is pressed onto the silicone adhesive such that the cloth becomes affixed to the acetate sheet. This is allowed to dry. In the next step, this sheet of acetate/cloth is laid on a flat surface with the cloth side up. Molds such as rubber washers purchased from a hardware store are laid on the cloth surface and filled with heated, liquefied gel (Memory Gel®, Applied Elastomerics, Pacifica, Calif.). At this point, before the liquefied gel has cooled, the gel can be shaped by simply placing a small object such as a rubber ball on the exposed surface of the liquefied gel such that a depression is created in the gel. The size of this depression can vary, but should correspond to the size of common foot lesions such as bunions, Haglund's deformities, exostoses, and the like. Once the liquefied gel has cooled and re-gelled, the molds are removed and the gel pads are coated with talc. Next, individual gel pads along with the backing material of acetate and cloth are cut out of the large sheet structure. My method involves placing an ostomy punch which is larger in diameter than the gel over the gel pad and pressing down such that a circular segment of acetate/cloth backing material along with the gel pad is removed. Ideally, the backing material should be larger in diameter than the gel pad such that a 1.00 mm to 10.0 mm border of backing material extends beyond the periphery of the gel pad. This protects the adhesive bandage from the oil in the gel when pressure or shearing forces are applied to the gel pad. The next step involves coating the surface of the bandage where the gel pad/backing sheet are to be affixed with silicone adhesive. The surface of the acetate backing sheet opposite the surface with the gel and fabric is then positioned onto the silicone adhesive on the fabric bandage, and the silicone adhesive is allowed to dry. The gel pad is thus secured to the adhesive Coverlet. The final step involves placing a small piece of the acetate sheeting material over the exposed surface of the gel so that the gel will be prevented from contacting surfaces such as a paper releasing sheet during storage and shipping which could result in bleeding of the oil from the gel.

RAMIFICATIONS AND VARIATIONS

Many oil-impervious barriers could be substituted for the acetate sheeting and flannel backing. The basic idea is to provide a barrier to prevent oil from the gel from bleeding onto the fabric bandage. Materials such as silicone rubber or plastic could be used to create this barrier. Such a material could be directly impregnated onto the fabric bandage rather than glued.

Figure 3:
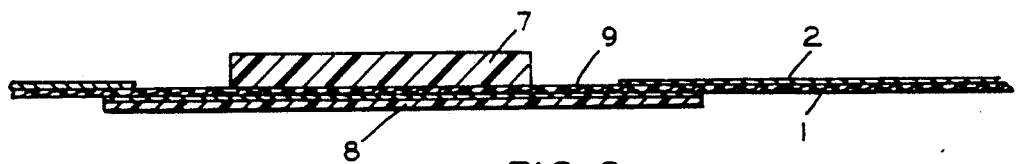
FIG. 3 is a sectional view of an alternative embodiment of the invention showing the gel pad directly impregnated onto the fabric of the bandage and the opposite surface of the bandage coated with a layer of oil impervious material.

Referring to FIG. 3, an alternative embodiment of the present invention is shown. An oil resistant material, such as silicone rubber for example, 8 is used to coat the exterior of the bandage 1, (i.e., the surface opposite the surface with the pressure sensitive adhesive 2), and the gel pad 7 is then directly impregnated onto the bare fabric of the fabric bandage 1. Ideally, there should be a border of bare fabric 9 between the gel pad and the pressure sensitive adhesive 2 such that the gel pad 7 and the pressure sensitive adhesive 2 would not come into contact when pressure was applied and the gel flattened out. This configuration would prevent oil from the gel from staining the socks, shoes, and the like.

Figure 4:
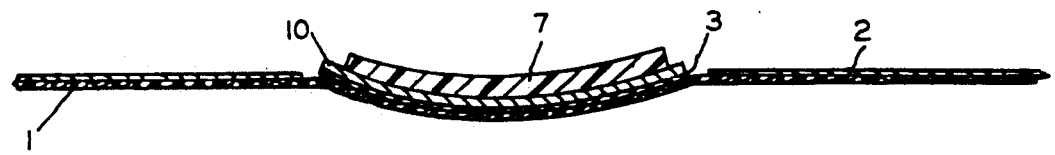
FIG. 4 is a sectional view of an alternative embodiment of the invention illustrating a semi-rigid backing member which provides a desirable contour to the device.

Referring to FIG. 4, yet another embodiment of the present invention is shown. A semi-rigid backing material 10 such as acetate, plastic, rubber, silicone, or the like is used and the backing material is preshaped to provide a contour to the finished pad. For example, the backing sheet 10 could be concavoconvex in shape with the gel pad affixed on the concave surface to produce a device that would fit over the convexity of a bunion or other protroberant orthopedic deformity. The method of impregnating the gel pad to the bandage could be essentially the same as described for the embodiment illustrated in FIGS. 1 and 2, or FIG. 3. Other means for securing the bandage to the foot would include elastic bands or sleeves which encircle a digit or the foot.

OPERATION OF THE INVENTION

The present invention is designed to dissipate pressure and shearing force exerted against the foot while softening and medicating keratotic lesions. To achieve these goals, the oleaginous gel pad 7 is applied directly against the foot and secured by means of the pressure sensitive adhesive 2 of the fabric bandage 1. When shoe-pressure is exerted against the ultrasoft gel the gel instantly begins to flow and conform to the contour of the foot and any orthopedic deformity therein. The viscoelastic gel pad dissipates the applied pressure throughout its mass in a fluid or "hydraulic" manner. This eliminates discrete pressure points or sharp pressure gradients that can occur in conventional foot padding materials such as felt or foam rubber. In addition, when external pressure is applied to the ultrasoft gel, the gel expands radially outward such that the surface area of the gel in contact with the foot increases. Spreading the applied pressure over a larger surface area of the foot results in lower force per unit of area against the foot. In order for a gel, or any material, to function in this manner it must be extremely elastic. The gelatinous composition taught by Chen in U.S. Pat. No. 4,369,284 can be stretched to sixteen times its resting length before tearing. This allows for greater spreading of the gel pad, and hence the applied pressure, over a much larger surface area than any viscoelastic material previously utilized in this art.

Extreme elasticity of the gel such as taught in U.S. Pat. No. 4,369,284 also allows the present inventions to function as a superior blister dressing. Even thin layers of gel, 1.00 mm or less are capable of internally absorbing the frictional forces exerted against the foot by shoegear. Much thicker layer of other known viscoelastic material would need to be employed to achieve equivalent results, an important consideration in the narrow confines of a shoe.

When utilizing a gel which possesses an oleaginous plasticizer or liquid fraction, the pad can also function as a medicator or drug delivery system. When the present invention employs Memory Gel ® according to the manner taught in this specification, Mineral Oil USP will naturally "bleed" onto the skin of the wearer. Mineral Oil USP has long been used in medicine and podiatry for its emollient properties. Corns, calluses, and the like are accretions of thick, hard, dried stratum cornium. When a coating of mineral oil is applied to such a keratotic lesion, moisture is retained by the skin and thus the lesion is softened. This results in less pain for the afflicted person and easier paring or trimming of the keratotic lesion. Pharmacologically active agents can also be incorporated into the oleaginous gel for delivery to the foot. For example, antifungal agents such as undecylenic acid, tolnaftate, miconazole, griseofulvin, ketoconazole, ciclopirox, clotrimazole, chloroxylenol and the like could be incorporated into the gel to discourage or eliminate the growth of dermatophytes. Keratolytic agents such as salicylic acid, lactic acid, or urea could be used to treat corns or calluses. Vessicants such as cantharidin or caustics such as podophyllin could be incorporated into the gel for destruction of warts. Similarly, antibiotics, antiperspirants, topical anesthetics, vitamins or antiinflammatories could be delivered to the foot via this drug deliver system. By providing an oil resistant barrier means, oil and/or medication is prevented from bleeding out of the device and fouling sock, shoes, or other articles of clothing. Alternatively, the sheet structure of the bandage may be made of an intrinsically oil resistant material.

Accordingly, the reader will see that the present invention is a novel and highly useful padding, friction dissipating, and medicating device for the human foot. By utilizing an oleaginous, viscoelastic, thermoplastic gel in combination with an adhesive coated bandage the present invention teaches a foot protective device that can simultaneously protect, pad, and medicate a pedal lesion and additionally teaches several embodiments and methods of manufacture for the same. Although the description above contains many specificities, these should not be construed as limiting the scope of the invention but merely providing illustrations of some of the present preferred embodiments of the invention. For example, the pad can be made from other viscoelastic substances which may not strictly speaking be "gels" but posses similar ultrasoft elastic qualities Likewise, the choice of gels may differ and encompass non-thermoplastic or non-oleoginous gels with the desirable features described above. Other methods of manufacture that lend themselves to mass-production may also be employed to achieve equivalent results.

The present invention can even be further simplified by eliminating the sheet structure and pressure sensitive adhesive and simply molding foot protective and medicating devices from a viscoelastic composition such as taught by Chen in U.S. Pat. No. 4,369,284. For example, this thermoplastic gelatinous composition could be cast in the shape of a toe spacer, crest pad, heel cup, corn or bunion pad, or any like orthopedic appliance known to this art. Such a device would be held in position by gravity, shoe/sock pressure, tape or opposing body (digital) surfaces.

Thus, the scope of the invention should be determined by the appended claims and their legal equivalents, rather than by the examples given.

I claim:

1. A padding and medicating device for the human foot, comprising:
    a. a layer of flexible material which is impervious to oil;
    b. a layer of permeable material attached to said layer of oil-impervious material; and
    c. a layer of gelatinous viscoelastic padding material having an oleaginous plasticizer fraction derived from petroleum, said padding material being impregnated onto said layer of permeable material.

2. The padding and medicating device, as recited in claim 1, wherein said layer of material which is impervious to oil is formed to include a peripheral border which extends beyond the gelatinous viscoelastic padding material, said peripheral border accommodating an increased dimension of the gelatinous viscoelastic padding material as created by external pressure thereupon.

3. The padding and medicating device, as recited in claim 1, wherein the layer of gelatinous viscoelastic padding material is attached to the layer of permeable material directly opposing the layer of oil-impervious material.

4. The padding and medicating device, as recited in claim 1, wherein the gelatinous viscoelastic padding material is a thermoplastic and is impregnated onto said layer of permeable material by thermoplastic means.

5. The padding and medicating device, as recited in claim 1, wherein said oleaginous plasticizer fraction derived from petroleum contains a pharmacologically active substance.

6. The padding and medicating device, as recited in claim 1, wherein said oleaginous plasticizer fraction derived from petroleum is Mineral Oil U.S.P.

7. The padding and medicating device, as recited in claim 1, wherein said padding material varies in thickness.

8. The padding and medicating device, as recited in claim 1, wherein said padding material is of uniform thickness.

9. A padding and medicating device for the human foot, comprising:
    a. a sheet of flexible fabric;
    b. a layer of material which is impervious to oil and is attached to said layer of flexible fabric;
    c. a layer of permeable material which is attached to said layer of oil-impervious material; and
    d. a layer of gelatinous viscoelastic padding material having an oleaginous plasticizer fraction derived from petroleum, said padding material being impregnated onto said layer of permeable material.

10. The padding and medicating device, as recited in claim 9, wherein the sheet of flexible fabric is elastic in nature.

11. The padding and medicating device, as recited in claim 9, wherein the layer of oil-impervious material is semi-rigid so as to impart a contour to said device.

12. The padding and medicating device, as recited in claim 1, wherein the oleaginous plasticizer fraction derived from petroleum is a liquid hydrocarbon having from 15 to 24 carbon atoms per molecule.

* * * * *